US008816109B2

(12) United States Patent
Bethala et al.

(10) Patent No.: US 8,816,109 B2
(45) Date of Patent: Aug. 26, 2014

(54) PROCESS FOR PREPARATION OF HEXADECYL CIS-9-TETRADECENOATE AND HEXADECYL CIS-10-TETRADECENOATE

(75) Inventors: Lakshmi Anu Prabhavathi Devi Bethala, Hyderabad (IN); Nadpi Gangadhar Katkam, Hyderabad (IN); Vijayalakshmi Kunkuma, Hyderabad (IN); Ramakrishna Sistla, Hyderabad (IN); Madhusudhana Kuncha, Hyderabad (IN); Vamanrao Diwan Prakash, Hyderabad (IN); Badari Narayana Prasad Rachapudi, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 490 days.

(21) Appl. No.: 13/144,260

(22) PCT Filed: Jan. 12, 2010

(86) PCT No.: PCT/IN2010/000021
§ 371 (c)(1),
(2), (4) Date: Jul. 12, 2011

(87) PCT Pub. No.: WO2010/079514
PCT Pub. Date: Jul. 15, 2010

(65) Prior Publication Data
US 2011/0269987 A1 Nov. 3, 2011

(30) Foreign Application Priority Data
Jan. 12, 2009 (IN) .............................. 45/DEL/2009

(51) Int. Cl.
C07C 69/533 (2006.01)
C12P 7/64 (2006.01)
C07C 67/02 (2006.01)
C11C 3/10 (2006.01)

(52) U.S. Cl.
CPC . *C07C 67/02* (2013.01); *C11C 3/10* (2013.01); *C12P 7/64* (2013.01); *C12P 7/649* (2013.01)
USPC ............................ 554/223; 560/217; 435/134

(58) Field of Classification Search
None
See application file for complete search history.

(56) References Cited

U.S. PATENT DOCUMENTS

| 4,113,881 | A | 9/1978 | Diehl | 514/549 |
| 4,409,824 | A | 10/1983 | Salama et al. | 73/152.48 |
| 5,569,676 | A | 10/1996 | Diehl | 514/549 |
| 2003/0181521 | A1 | 9/2003 | Leonard et al. | 514/552 |
| 2006/0062859 | A1 | 3/2006 | Blum et al. | 424/725 |
| 2007/0020254 | A1 | 1/2007 | Levin | 424/94.63 |

FOREIGN PATENT DOCUMENTS

WO  WO 00/64436  11/2000
WO  WO 01/41783  6/2001

OTHER PUBLICATIONS

Appel et al., "A Wittig Reaction with 2-Furyl Substituents at the Phosphorus Atom: Improved (Z) Selectivity and Isolation of a Stable Oxaphosphetane Intermediate," *Eur. J. Org. Chem.*, 2002(7)1143-1148, 2002.
Bestmann et al., "Pheromones. VII. Synthesis of 1-substituted (Z)-9-alkenes," *Chemische Berichte*, 108(11)3582-95, 1975. (German publication. English abstract).
Diehl et al., "Cetyl myristoleate isolated from Swiss albino mice: an apparent protective agent against adjuvant arthritis in rats," *Pharm. Sci.*, 83(3):296-299, 1994. (Abstract).
Edwards, "CMO (Cerasomol-cis-9-Cetyl Myristoleate) in the Treatment of Fibromyalgia: An Open Pilot Study," *J. Nutr. Environ. Med.*, 11:105-111, 2001.
Garcia Martinez et al., "A new type of anomalous ozonolysis in strained allylic bicycloalkan-1-ols," *Tetrahedron Letters*, 46(31):5157-5159, 2005.
Hunter et al, "Synthesis of cetyl myristoleate and evaluation of its therapeutic efficacy in a murine model of collagen-induced arthritis," *Pharmacological Research*, 47(1):43-47, 2003.
PCT International Preliminary Report on Patentability issued in International application No. PCT/IN2010/000021, dated Apr. 19, 2011.
PCT International Search Report and Written Opinion issued in International application No. PCT/IN2010/000021, dated Jun. 4, 2010.
Pearson et al., "Development of arthritis, periarthritis and periostitis in rats given adjuvant," *Proc. Soc. Exper. Biol. Med.*, 91:95-101, 1956.
Vinczer et al., "Simple and stereocontrolled synthesis of an optimal isomeric mixture of 3,13-octadecadien-1-YL acetates," *Synthetic Communications*, 15(14):1257-1270, 1985.
Vogel's Drug Discovery and Evaluation Pharmacological assays, 2nd Edition, Springer Verlag, Chaper 1, pp. 802-803, 2002.
Winter et al., "Anti-inflammatory and antipyretic activities of indomethacin, 1-(p-chlorobenzoyl)-5-methoxy-2-methylindole-3-acetic acid," *J. Pharmacolo. Exp. Ther.*, 141:369-376, 1963.

*Primary Examiner* — Yevegeny Valenrod
(74) *Attorney, Agent, or Firm* — Fulbright & Jaworski LLP (57) ABSTRACT

Hexadecyl cis-9-tetradecenoate commonly known as Cetyl myristoleate (CMO) is being used for the treatment of osteoarthritis and other joint inflammatory diseases, cis-9-Tetradecenoic acid (cis-9-myristoleic acid) is the main precursor for the preparation of CMO. As there are limited natural plant sources for cis-9-tetradecenoic acid, the present invention aimed at the synthesis of cis-9-tetradecenoic acid methyl ester from oleic acid methyl ester. As oleic acid is not available in pure form, this has to be isolated from oleic acid-rich oils like olive oil. cis-10-Tetradecenoic acid methyl ester, an isomer of cis-9-tetradecenoic acid was also prepared from undecenoic acid methyl ester, a derivative of castor oil. Undecenoic acid is easily available commercially in pure form. Hexadecyl cis-9-tetradecenoate and hexadecyl c/s-10-tetradecenoate were prepared by enzymatic transesterification of cis-9-tetradecenoic acid methyl ester and cis-10-tetradecenoic acid methyl ester with 1-hexadecanol (cetyl alcohol) respectively. Both the isomers of cetyl myristoleate were evaluated for anti arthritis, blocking inflammation and reduction of adjuvant-induced arthritis in rats.

8 Claims, 5 Drawing Sheets

PROCESS FOR PREPARATION OF HEXADECYL CIS-9-TETRADECENOATE AND HEXADECYL CIS-10-TETRADECENOATE

This application is a national phase application under 35 U.S.C. §371 of International Application No. PCT/IN2010/000021 filed 12 Jan. 2010, which claims priority to Indian Application No. 45/DEL/2009 filed 12 Jan. 2009. The entire text of each of the above-referenced disclosures is specifically incorporated herein by reference without disclaimer.

FIELD OF THE INVENTION

The present invention relates to a process for the preparation of two isomers of cetyl myristoleate namely hexadecyl cis-9-tetradecenoate and hexadecyl cis-10-tetradecenoate. More particularly, the present invention also relates to evaluation of both the isomers hexadecyl cis-9-tetradecenoate and hexadecyl cis-10-tetradecenoate for blocking inflammation and reduction of adjuvant-induced arthritis in rats.

BACKGROUND OF THE INVENTION

Cetyl myristoleate (CMO) is the common name for hexadecyl cis-9-myristoleate. CMO is the ester of cis-9-tetradecenoic acid (myristoleic acid) and 1-hexadecanol (cetyl alcohol). Cetyl myristoleate is well known for its anti arthritis properties. Hexadecyl cis-9-tetradecenoate was found only in very selective number of species of animals including cows, whales, beavers and mice. Cetyl myristoleate was isolated from mice in 1972 by Harry W. Diehl, a researcher at the National Institutes of Health (Diehl H W, May E L. J Pharm Sci 1994; 83:296-9). Cetyl myristoleate has been used for immunizing against inflammatory rheumatoid arthritis in mammals (Diehl, U.S. Pat. No. 4,049,824, Levin, WO 01/41783), treatment of rheumatoid arthritis (Diehl, U.S. Pat. No. 4,113,881) and osteoarthritis (Diehl, U.S. Pat. No. 5,569,676). Vegetable butter-based cetyl myristoleate was also used for treating osteoarthritis and other musculoskeletal disease conditions and injuries (Leonard, US 20030181521). Nutraceuticals containing CMO are widely used for reducing pain inflammation, and with the exception of a report suggesting a positive clinical effect of cerasomol-CMO in patients with fibromyalgia (Edwards A M. J. Nutr. Environ. Med. 2001; 11:105-11). As Swiss Albino Mice is the only natural source for CMO, Kenneth et al, synthesized pure hexadecyl cis-9-tetradecenoate by esterifying cis-9-tetradecenoic acid (purchased from commercial source) with 1-hexadecanol by chemically and confirmed its anti arthritic properties in a collagen-induced arthritis model in DBA/1 Lac J mice (Kenneth W. Hunter, Jr., Ruth A. Gault, Jeffrey S. Stehouwer, Suk-Wah Tam-Chang. Pharmacological Research 2003; 47:43-47). cis-9-Myristoleic acid is naturally available as a mixture of fatty acids along with other fatty acids in beef tallow fat with cis-9-myristoleic acid content of 8% (Lord G, WO 00/64436) and seed fat of Pycnanthus Komb with 20-30% of cis-9-myristoleic acid (Leonard, US 20030181521). Literature search revealed that there is no synthetic route reported for the preparation of cis-9-myristoleic acid. Since the natural availability of cis-9-myristoleic acid is scarce, the present invention reported synthetic route for the first time from methyl oleate. As it is difficult to isolate pure oleic acid from any vegetable oil source, the present invention reported the synthesis of a new isomer cis-10-myristoleic acid for the first time from commercially available raw material namely, undecenoic acid. Cetyl myristoleate was then prepared by transesterifying both methyl cis-10-myristoleate and cis-9-myristoleate separately with cetyl alcohol and evaluated for anti-inflammatory and anti-arthritis activity. The anti-inflammatory and anti-arthritis properties of the new isomer i.e. cetyl cis-10-myristoleate was compared with that of known CMO containing cis-9-myristoleic acid prepared as described above.

The first step of the synthetic route is preparation of cis-9-myristoleic acid from oleic acid. Oleic acid is not available in pure form, and has to be prepared from oleic acid-rich oils like olive oil by employing methodologies like urea adducts or fractional distillation. As the isolation of pure oleic acid from natural sources is very expensive, the cost of cetyl myristoleate based on cis-9 myristoleic acid will also be very high. Hence, there is a need for the identification of an alternate source of myristoleic acid for the preparation of CMO. Surprisingly, not much work was reported in this direction either for the chemical synthesis of cis-9 myristoleic acid or any other alternate raw material for the preparation of CMO. Keeping these points in view, the present invention explored the possibility of synthesis of alternative isomers of myristoleic acid, for the preparation of cetyl myristoleate. An attractive substrate in this direction is 10-undecenoic acid for the preparation of cis-10 myristoleic acid. 10-Undecenoic acid is a pyrolysis product of castor oil fatty acid methyl esters (methyl ricinoleate) and is commercially available in bulk in pure form. In the present invention, both the isomers of methyl esters of cis-9 and cis-10 myristoleic acids (3 and 7) were prepared from oleic and undecenoic acid methyl esters and further transesterified with cetyl alcohol to obtain hexadecyl cis-9-tetradecenoate, 4 and hexadecyl cis-10-tetradecenoate, 8. Both hexadecyl cis-9-tetradecenoate, 4 and hexadecyl cis-10-tetradecenoate, 8 were evaluated for anti-arthritis properties and found that hexadecyl cis-10-tetradecenoate, 8 is comparable with that of hexadecyl cis-9-tetradecenoate, 4 in inhibiting inflammation and effective in adjuvant-induced arthritis in rats.

OBJECTIVES OF THE INVENTION

The main objective of the present invention is to provide a process for the preparation of two isomers of cetyl myristoleate namely hexadecyl cis-9-tetradecenoate and hexadecyl cis-10-tetradecenoate.

Still another objective of the present invention is evaluation of both the isomers hexadecyl cis-9-tetradecenoate and hexadecyl cis-10-tetradecenoate for blocking inflammation and reduction of adjuvant-induced arthritis in rats.

SUMMARY OF THE INVENTION

Accordingly, the present invention provides a process for the preparation of two isomers of cetyl myristoleate namely hexadecyl cis-9-tetradecenoate and hexadecyl cis-10-tetradecenoate and evaluation of both the isomers hexadecyl cis-9-tetradecenoate and hexadecyl cis-10-tetradecenoate for blocking inflammation and reduction of adjuvant-induced arthritis in rats In an embodiment of the present invention a process for the preparation of two isomers of cetyl myristoleate namely hexadecyl cis-9-tetradecenoate and hexadecyl cis-10-tetradecenoate having general formula 1, General formula 1

Where n = 7 or 8
Where m = 3 or 2 comprising the steps of:
a. cooling of an ester selected from the group consisting of oleic acid methyl ester and methyl undecenoate in the presence of an organic solvent at temperature ranges between −70 to −78° C.;
b. ozonolysis of cooled ester by bubbling of ozone for a period ranging between 60-90 min;
c. quenching the reaction with dimethyl sulphide (DMS) followed by stirring for a period ranging between 6-8 hr at temperature ranging between 25-35° C.;
d. evaporating the solvent and DMS from the reaction mixture as obtained in step (c) under vacuum to get crude solid containing 1-al-methyl nonoate or 1-al-methyl deaconate depending upon the ester used in step (a);
e. dissolving crude solid containing 1-al-methylalkyloate as obtained in step (d) in dry THF (tetra hydro furan);
f. simultaneously, dissolving triphenyl phosphine salt selected from the group consisting of n-pentyl-triphenyl phosphonium salt and n-butyl-triphenyl phosphonium salt in dry THF and cooled to a temperature ranging between 0-5° C. and followed by addition of n-butyl lithium;
g. stirring the reaction mixture as obtained in step (f) for a period ranging between 30-60 min to obtain an orange solution;
h. adding solution of crude solid in dry THF as obtained in step (e) into the solution of triphenyl phosphine salt in dry THF as obtained in step (f) followed by refluxing for a period of 3-8 hrs;
i. removing THF from the reaction mixture as obtained in step (h) under reduced pressure to get residue;
j. adding water in the residue as obtained in step (i) and followed by extraction with ether;
k. removing ether under vacuum to get the residue followed by carrying out purification using column chromatography using hexane and ethyl acetate (98:2) as eluent to get cis-9-myristoleate and cis-10-myristoleate depending upon the ester used in step (a) and triphenyl phosphine salt used in step (f);
l. transesterifying myristoleate as obtained in step (k) with cetyl alcohol in the presence of enzyme selected from the group consisting of Lipozyme TL IM and Novozyme 435 at temperature ranging between 65-70° C. for a period ranging between 8 to 10 hr;
m. separating enzyme by filtration and evaporating the solvent to get the crude product having respective isomer of cetyl myristoleate;
n. purifying the crude product as obtained in step (l) by column chromatography to obtain pure cetyl, myristoleate of formula 1.

In another embodiment of the present invention a process, wherein the solvent used in step (a) is dichloromethane or chloroform.

In another embodiment of the present invention oleic acid methyl ester used in step (a) and n-pentyl-triphenyl phosphonium salt used in step (f) for the preparation of cis-9-tetradecenoate.

In another embodiment of the present invention methyl undecenoate used in step (a) and n-butyl-triphenyl phosphonium salt used in step (f) for the preparation of cis-10-tetradecenoate.

In another embodiment of the present invention hexadecyl cis-9-tetradecenoate yielded in the range of 88-95%.

In another embodiment of the present invention hexadecyl cis-9-tetradecenoate purity is in the range of 92-95%.

In another embodiment of the present invention hexadecyl cis-10-tetradecenoate yielded in the range of 80-90%.

In another embodiment of the present invention hexadecyl cis-10-tetradecenoate purity is in the range of 90-95%.

In another embodiment of the present invention the said isomers hexadecyl cis-9-tetradecenoate and hexadecyl cis-10-tetradecenoate as prepared are evaluated for blocking inflammation and reduction of adjuvant-induced arthritis in rats.

In another embodiment of the present invention use of isomers hexadecyl cis-9-tetradecenoate and hexadecyl cis-10-tetradecenoate for blocking inflammation and reduction of adjuvant-induced arthritis.

In another embodiment of the present invention use of isomers for blocking inflammation, wherein the isomers hexadecyl cis-9-tetradecenoate and hexadecyl cis-10-tetradecenoate are effective to reduce the inflammation and edema of the animals equally up to 36% compared to control group at a dose 400 mg/kg body wt.

In another embodiment of the present invention use of isomers for reduction of adjuvant-induced arthritis activity, wherein the isomers hexadecyl cis-9-tetradecenoate and hexadecyl cis-10-tetradecenoate are effective to reduce arthritis equally up to 10 to 15% at the dose of 100 mg/kg body wt.

In another embodiment of the present invention use of isomers for anti-arthritic activity, wherein the isomer hexadecyl cis-10-tetradecenoate is effective for 21 days in 80% rats while in 20% rats it is effective for 32 days.

DETAILED DESCRIPTION OF THE INVENTION

Figure 1:
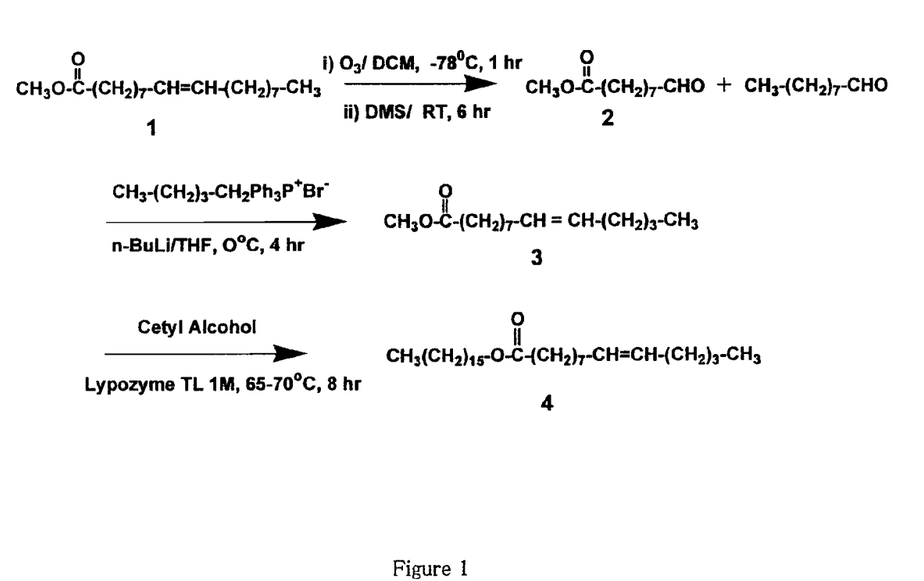
FIG. 1: Scheme 1: Preparation of Hexadecyl cis-9-Tetradecenoate
Figure 2:
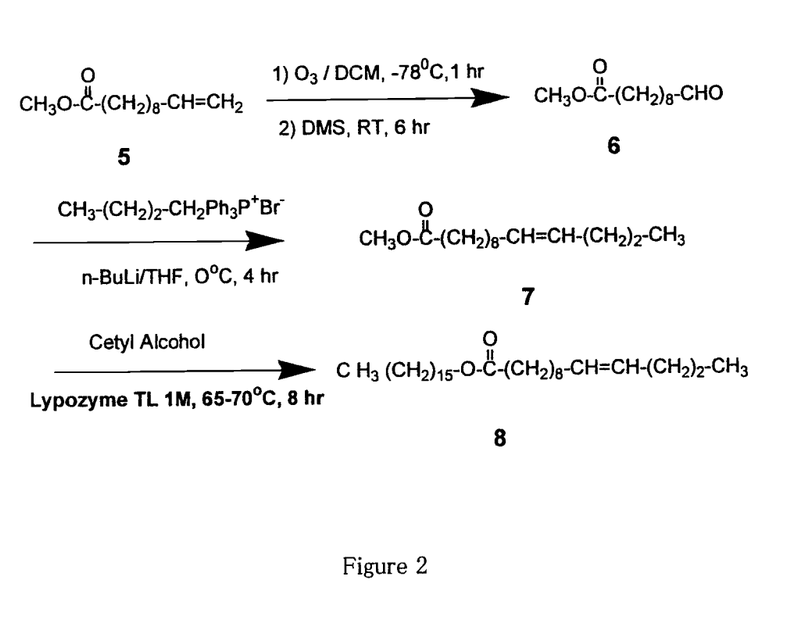
FIG. 2: Scheme 2: Preparation of Hexadecyl cis-10-Tetradecenoate

The present invention relates to the synthesis of two isomers of cetyl myristoleate namely hexadecyl cis-9-tetradecenoate, 4 and hexadecyl cis-10-tetradecenoate, 8 according to Scheme 1 and Scheme 2. The main component of CMO is cis-9 myristoleic acid, and is being isolated from selective natural sources along with other fatty acids. The literature reveals that there is no source, which can provide pure cis-9 myristoleic acid. Only solution to address this problem is its chemical synthesis starting from oleic acid. As the isolation of pure oleic acid from natural sources like olive or any other vegetable oils is very expensive, the cost of cetyl myristoleate based on cis-9 myristoleic acid will also be very high. Hence, there is a need for the identification of an alternate source of myristoleic acid for the preparation of CMO. An attractive substrate in this direction is 10-undecenoic acid for the preparation of cis-10 myristoleic acid. 10-Undecenoic acid is a pyrolysis product of castor oil fatty acid methyl esters (methyl ricinoleate) and is commercially available in pure form. Hence, in the present invention synthesis of two isomers namely cis-9-tetradecenoic acid methyl ester, 3 and cis-10-tetradecenoic acid methyl ester, 7 were prepared from methyl esters of oleic and 10-undecenoic acid respectively. The synthesis of 3 and 7 involves ozonolysis (Santiago de la Moya et al. Tetrahedron Letters 2005; 46:5157-5159) of oleic acid and undecenoic acid methyl esters to get 1-al-methylnonoate, 2 and 1-al-methyldecanoate 6. These aldehydes were subjected to Wittig reaction [Marco Appel, Steffen Blaurock, Stefan Berger. Eur. J. Org. Chem. 2002; 1143-1148] with triphenyl phosphine salt of n-pentyl and n-butyl bromide prepared according to Peter et al., [Peter Vinczer, Gabor Baan, Zoltan Juvancz, Lajos Novak, and Csaba Szantay, Synthetic Communications 1985; 15(14):1257-1270] to get cis-9-myristoleate, 3 and cis-10-myristoleate, 7 and were subjected to enzymatic transesterification with cetyl alcohol using lipozyme TL IM to obtain hexadecyl cis-9-tetradecenoate, 4 and hexadecyl cis-10-tetradecenoate, 8. Both these compounds were evaluated for anti arthritis properties and found that hexadecyl cis-10-tetradecenoate, 8 is comparable with that of hexadecyl cis-9-tetradecenoate, 4 in inhibiting inflammation and effective in adjuvant-induced arthritis in rats.

The synthesis of hexadecyl cis-9-tetradecenoate, 4 was carried out as shown in Scheme 1, comprising ozonolysis of oleic acid methyl ester, 1 [prepared by esterification of oleic acid (>98% purity) with 2% sulfuric acid/methanol] using dichloromethane as solvent, at −78 degree C. for 1 hr. The reaction was quenched with dimethyl sulphide (DMS) and continued the stirring for 6 hr. The solvent and DMS from the reaction mixture was evaporated and dried under vacuum. The product thus obtained was rich in 1-al-methylnonoate, 2 along with 1-nonanal (C-9 aldehyde) and the same was subjected to Wittig reaction with triphenyl phosphine salt of n-pentyl bromide in n-BuLi/THF to get cis-9-myristoleate, 3 in 55-65% yield with 66-70% purity. The cis-9-myristoleate, 3 was transesterified with cetyl alcohol using either 1,3-specific or non-specific lipases like Lipozyme TL IM (*Thermomyces lanuginosa*) and Novozyme 435 (*Candida antarctica*) at 65° C. to 70° C. for 8 hr to get hexadecyl cis-9-tetradecanoate, 4 in 88-95% yield with 92-95% purity. The purity of all the products was checked by GC and the structures were confirmed by GC-MS, IR and $^1$H NMR.

The synthesis of hexadecyl cis-10-tetradecenoate, 8 was carried out as shown in Scheme 2, ozonolysis of 10-undecenoic acid methyl ester, 5 (>99% pure) using dichloromethane as solvent at −78° C. for 1 hr. The reaction was quenched with dimethyl sulphide (DMS) and continued the stirring for 6 hr. The solvent and DMS from the reaction mixture was evaporated and dried under vacuum to get 1-al-methyldecanoate, 6 in 90% yield. The crude aldehyde, 6 was subjected to Wittig reaction with triphenyl phosphine salt of n-butyl bromide in n-BuLi/THF to get cis-10-myristoleate, 7 in 65-68% yield with 75-78% purity. The cis-10-myristoleate, 7 was transesterified with cetyl alcohol using Lipozyme TL IM at 65° C. to 70° C. for 8 hr to get hexadecyl cis-10-tetradecanoate, 8 in 88-90% yield with 90-95% purity. The purity of all the products was checked by GC and the structures were confirmed by GC-MS, IR and $^1$H NMR.

The anti-inflammatory activity potential of both the isomers of the cetyl myristoleate (4 & 8) was evaluated initially in carrageenan induced rat paw edema model employing the method of Winter et al (Winter C A, Risley E A and Nuss G W, J. Pharmacolo. Exp. Ther. 1963; 141:369-376). The arthritis developed by injecting Freund's Complete Adjuvant in Wistar rats is almost similar to the rheumatoid arthritis of the human beings. Hence, further studies on anti-arthritic activity were done employing the method of Pearson et. al (Pearson C M, Proc. Soc. Exper. Biol. Med. 1953; 91:95-101). The studies of anti-arthritis properties were evaluated for both the isomers of cetyl myristoleates and found that hexadecyl cis-10-tetradecenoate, 8 was also comparable with that of hexadecyl cis-9-tetradecenoate, 4 in inhibition of inflammation and reduction of adjuvant-induced arthritis in rats.

Example 1

Preparation of Hexadecyl cis-9-Tetradecenoate: Preparation of hexadecyl cis-9-tetradecenoate, 4 was carried out according to the Scheme 1. Oleic acid methyl ester, 1 (12.0 g, 0.0314 mol) in dichloromethane (100 ml) was cooled to −78 degree. C and ozone gas was bubbled into the reaction mixture for 1 hr. After reaction, the reaction was quenched by adding dimethyl sulphide (DMS, 8 ml) and was stirred for 6 hr at 25° C. The solvents were removed under vacuum and the residue 2 thus obtained (4.25 g, 0.022 mol) was used directly for the preparation of cis-9-myristoleate, 3. n-Pentyl-triphenyl phosphonium salt (11.16 g, 0.027 mol) was taken in 50 ml of dry THF and cooled to 0° C. To this slurry, n-butyl lithium (17.0 ml, 1.6 M in hexane) was added, stirred the reaction mixture for 0.5 hr to obtain an orange solution. 1-Al-methyl nonanoate containing crude product 2 (5.0 g, 0.027 mol) dissolved in dry THF (20 ml) was added to the above contents slowly and allowed the reaction mixture to reach to 25 degree. C and then heated to reflux temperature to reflux for 4 hr. The reaction was monitored by TLC and after completion of the reaction, THF was removed from the reaction mixture under reduced pressure, and to the residue distilled water 825 ml) was added and extracted with ether (25 ml×3 times). The combined ether layer was dried over anhydrous sodium sulphate and solvent was removed and dried under vacuum to get the residue and was purified by column chromatography using hexane and ethyl acetate (98:2) as eluent to get cis-9-myristoleate, 3 (4.2 g, 0.0175 mol) in 65% yield with 66% purity by GC. cis-9-Myristoleate, 3 (4.2 g, 0.0175 mol) was enzymatically transesterified with cetyl alcohol (5.08 g 0.021-mol) in the presence of Lipozyme TL IM (0.930 g, 10 wt % of the total substrate) at 68° C. for 8 hr. The reaction was monitored by TLC and after completion of the reaction, hexane (50 ml) was added and the lipase was separated by filtration and the solvent was evaporated to get the crude product and was purified by column chromatography to obtain hexadecyl cis-9-tetradecenoate, 4 (7.48 g, 0.0166 mol) in 95% yield with 92% purity by GC. The structure of hexadecyl cis-9-tetradecenoate, 4 was confirmed by $^1$H NMR, IR, and GC-MS.

Spectral Data:

$^1$H NMR: (600 MHz, CDCl$_3$): δ 5.36-5.33 (m, 2H, J=3 Hz, —CH=CH—), 4.01

1.99 (m, 4H, —CH$_2$—CH=CH—CH$_2$—), 1.60 (m, 4H, —CH$_2$—CH$_2$—CH=CH—CH$_2$—CH$_2$—), 1.30-1.20 (br, d, 38H, —CH$_2$—CH$_2$—CH$_2$—), 0.90 (q, 6H, —CH$_2$—CH$_3$).

IR (neat/NaCl): 2926, 1738, 1654, 1242, 721 Cm$^{-1}$.

GC-MS: m/z: C$_{30}$H$_{58}$O$_2$ (M$^+$): 450.

Example 2

Preparation of Hexadecyl cis-9-Tetradecenoate: cis-9-Myristoleate, 3 (4.2 g, 0.0175 mol) was enzymatically transesterified with cetyl alcohol (5.08 g, 0.021 mol) in the presence of Novozyme 435 (0.930 g, 10 wt % of the total substrate) at 68° C. for 8 hr. The reaction was monitored by TLC and after completion of the reaction, hexane (50 ml) was added and the lipase was separated by filtration and the solvent was evaporated to get the crude product and was purified by column chromatography to obtain hexadecyl cis-9-tetradecenoate, 4 (7.48 g, 0.0166 mol) in 90% yield with 90% purity by GC. The structure of hexadecyl cis-9-tetradecenoate, 4 was confirmed by $^1$H NMR, IR, and GC-MS.

Spectral Data:
$^1$H NMR: (600 MHz, CDCl$_3$): δ 5.36-5.33 (m, 2H, J=3 Hz, —C$\underline{H}$=C$\underline{H}$—), 4.01

1.99 (m, 4H, —C$\underline{H}_2$—CH=CH—C$\underline{H}_2$—), 1.60 (m, 4H, —C$\underline{H}_2$—CH$_2$—CH=CH—CH$_2$—C$\underline{H}_2$—), 1.30-1.20 (br, d, 38H, —CH$_2$—C$\underline{H}_2$—CH$_2$—), 0.90 (q, 6H, —CH$_2$—C$\underline{H}_3$).
IR (neat/NaCl): 2926, 1738, 1654, 1242, 721 Cm$^{-1}$.
GC-MS: m/z: C$_{30}$H$_{58}$O$_2$ (M$^+$): 450.

Example 3

Preparation of Hexadecyl cis-10-Tetradecanoate: Preparation of hexadecyl cis-10-tetradecenoate, 8 was carried out according to the Scheme 2. Methyl undecenoate, 5 (10.21 g, 0.0515 mol) in dichloromethane (150 ml) was cooled to –78° C. and ozone gas was bubbled into the reaction mixture for 1 hr. The reaction was quenched by adding dimethyl sulphide (DMS, 5 ml) and was stirred for 6 hr at 25° C. The solvents were removed under vacuum and the residue 6 thus obtained was used directly further preparation of cis-10-myristoleate, 7. n-Butyl-triphenyl phosphonium bromide salt (10.0 g, 0.0251 mol) was taken in dry THF (50 ml) and cooled to 0° C. To this slurry, n-Butyl lithium (17.0 ml, 1.6 M in hexane) was added and stirred for 0.5 hr. 1-Al-methyl deaconate containing crude product 6 (5.01 g, 0.025 mol) dissolved in dry THF (50 ml) was added slowly to the above contents and allowed the reaction mixture to warm to roam temperature and then heated to reflux temperature to reflux for 4 hr. THF was removed from the reaction product under reduced pressure, and to the residue distilled water (25 ml) was added and extracted with ether (25 ml×3 times). The combined ether layer was dried over anhydrous sodium sulphate and solvent was evaporated and dried under vacuum to get the product and was further purified by column chromatography using hexane and ethyl acetate (98:2) as eluent to obtain cis-10-myristoleate, 7 (3.35 g, 0.014 mol) in 56% yield with 97% purity by GC. cis-10-Myristoleate, 7 (3.35 g, 0.014 mol) was enzymatically transesterified with cetyl alcohol (4.07 g, 0.0168 mol) in the presence of Lipozyme TL IM (0.745 g, 10 wt % of the total substrate), at 65° C. for 8 hr. The reaction was monitored by TLC and after completion of reaction, hexane (50 ml) was added and the lipase, was separated by filtration and the solvent was evaporated to get the crude product and was purified by column chromatography to obtain hexadecyl cis-10-tetradecenoate, 8 (5.55 g, 0.0123) in 88% yield with 95% purity by GC. The structure of hexadecyl cis-10-tetradecenoate, 8 was confirmed by $^1$H NMR, IR, and GC-MS.

Spectral Data:
$^1$H NMR (600 MHz, CDCl$_3$): δ 5.30 (m, 2H, —C$\underline{H}$=C$\underline{H}$—), 4.01

2.0 (m, 4H, —C$\underline{H}_2$—CH=CH—C$\underline{H}_2$—) 1.60 (m, 4H, —C$\underline{H}_2$—CH$_2$—CH=CH—CH$_2$—C$\underline{H}_2$—), 1.30-1.20 (br, d, 38H, —CH$_2$—C$\underline{H}_2$—CH$_2$—), 0.90 (q, 6H, —CH$_2$—C$\underline{H}_3$).
IR (neat/NaCl): 2926, 1738, 1654, 1242, 721 Cm$^{-1}$.
GC-MS: m/z: C$_{30}$H$_{58}$O$_2$ (M$^+$): 450.

Example 4

Preparation of Hexadecyl cis-10-Tetradecanoate: cis-10-Myristoleate, 7 (3.35 g, 0.014 mol) was enzymatically transesterified with cetyl alcohol (4.07 g, 0.0168 mol) in the presence of Novozyme 435 (0.745 g, 10 wt % of the total substrate), at 65 degree. C for 8 hr. The reaction was monitored by TLC and after completion of reaction, hexane (50 ml) was added and the lipase was separated by filtration and the solvent was evaporated to get the crude product and was purified by column chromatography to obtain hexadecyl cis-10-tetradecenoate, 8 (5.55 g, 0.0123) in 80% yield with 90% purity by GC. The structure of hexadecyl cis-10-tetradecenoate, 8 was confirmed by $^1$H NMR, IR, and GC-MS.

Spectral Data:
$^1$H NMR (600 MHz, CDCl$_3$): δ 5.30 (m, 2H, —C$\underline{H}$=C$\underline{H}$—), 4.01

2.0 (m, 4H, —C$\underline{H}_2$—CH=CH—C$\underline{H}_2$—), 1.60 (m, 4H, —C$\underline{H}_2$—CH$_2$—CH=CH—CH$_2$—C$\underline{H}_2$—), 1.30-1.20 (br, d, 38H, —CH$_2$—C$\underline{H}_2$—CH$_2$—), 0.90 (q, 6H, —CH$_2$—C$\underline{H}_3$).
IR (neat/NaCl): 2926, 1738, 1654, 1242, 721 Cm$^{-1}$.
GC-MS: m/z: C$_{30}$H$_{58}$O$_2$ (M$^+$): 450.

Example 5

Figure 3:
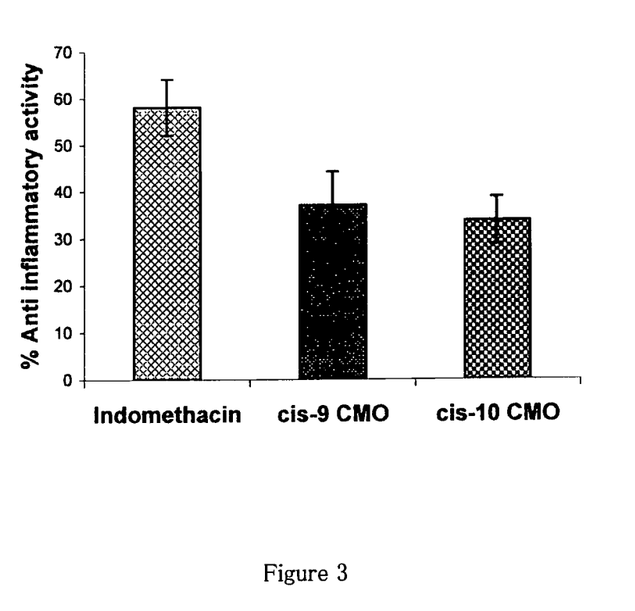
FIG. 3: Anti-inflammatory activity of Hexadecyl cis-9-Tetradecenoate (cis-9 CMO) and Hexadecyl cis-10-Tetradecenoate (cis-10 CMO)

Evaluation Studies of Hexadecyl cis-9-Tetradecenoate and Hexadecyl cis-10-Tetradecenoate for Anti-inflammatory. Potential: Hexadecyl cis-9-tetradecenoate, 4 and hexadecyl cis-10-tetradecenoate, 8 produced synthetically exemplified above in Scheme 1 and Scheme 2 were assessed for the anti-inflammatory potential against carrageenan induced paw edema model. Rats were divided into 4 groups. Hexadecyl cis-9-tetradecenoate, 4. and hexadecyl cis-10-tetradecenoate, 8 were administered intraperitoneally to rats in two different groups at a dose of 400 mg/kg. Another test group received indomethacin at a dose of 10 mg/kg, which is used as reference standard. Control group received vehicle alone. One hour after the administration of test compounds carrageenan (1%, 0.1 ml) was injected into the sub plantar region of animals in all the groups. Paw volumes were measured using plethysmometer before injecting carrageenan. Paw volumes were again measured 3 hr after the carrageenan administration. The anti-inflammatory potential of hexadecyl cis-9-tetradecenoate, 4 and hexadecyl cis-10-tetradecenoate, 8 were assessed by measuring the inhibition of the paw volumes with reference to mean paw volume in control group. Both hexadecyl cis-9-tetradecenoate, 4 and hexadecyl cis-10-tetradecenoate, 8 were found to reduce the inflammation and edema of the animals equally up to 36% compared to control group (FIG. 3).

Example 6

Figure 4:
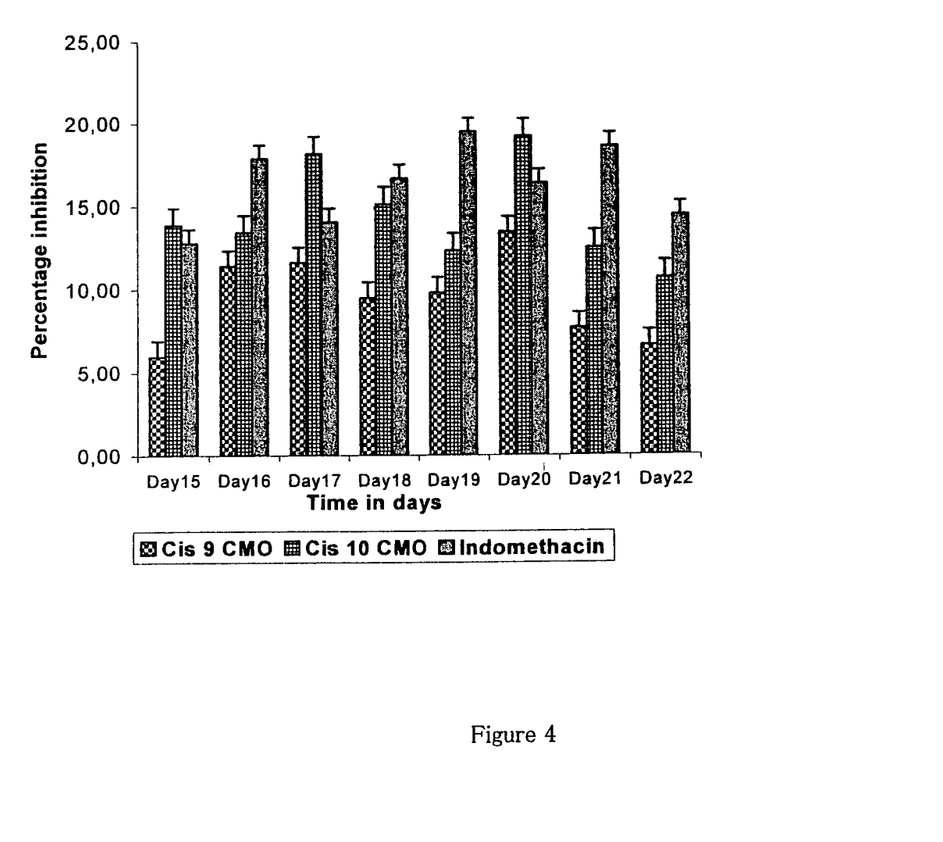
FIG. 4: Effect of Hexadecyl cis-9-Tetradecenoate (cis-9 CMO) and Hexadecyl cis-10-Tetradecenoate (cis-10 CMO) on the Arthritic Rats
Figure 5:
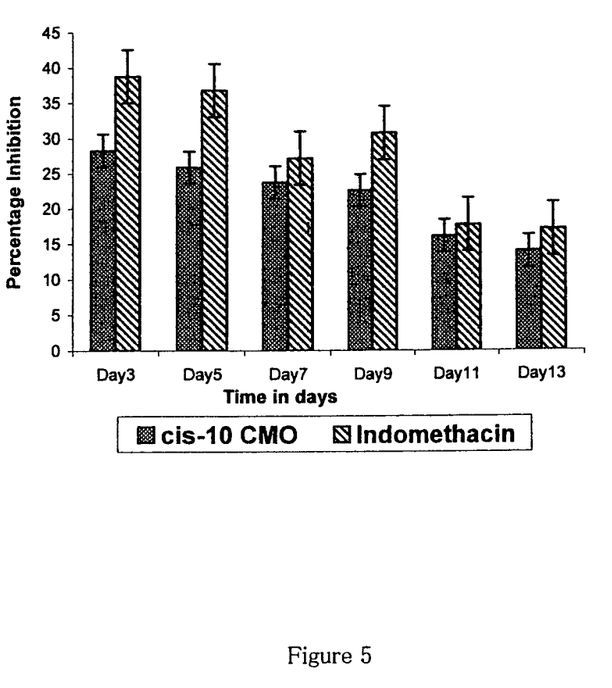
FIG. 5: Anti-arthritic Potential of Hexadecyl cis-10-Tetradecenoate (cis-10 CMO)

Effect of Hexadecyl cis-9-Tetradecenoate and Hexadecyl cis-10-Tetradecenoate on the Arthritic Rats: The hexadecyl cis-9-tetradecenoate, 4 and hexadecyl cis-10-tetradecenoate, 8 produced synthetically given above in Scheme 1 and 2 were subjected to evaluation for anti-arthritic potential in Freund's complete adjuvant induced arthritis model in rats. Male Wistar rats were divided into 4 groups each containing 6 rats. Arthritis was induced in rats in all the groups by administering Complete Freund's Adjuvant (CFA) at the dose of 1 mg per rat by injecting at sub plantar region of the right hind paw. Paw volumes were measured for both paws on every alternate day till 14 days and till full arthritis was developed. Hexadecyl cis-9-tetradecenoate, 4 (100 mg/kg/day), hexadecyl cis-10-tetradecenoate, 8 (100 mg/Kg/day) and indomethacin (2.5 mg/Kg/day were administered from $14^{th}$ day till $22^{nd}$ day. Paw volumes were again measured daily from $15^{th}$ day to $22^{nd}$ day for all rats in all groups. The percent inhibition of arthritis in the treated groups was calculated with reference to control group (FIG. 4). It was found that hexadecyl cis-9-tetradecenoate, 4 and hexadecyl cis-10-tetradecenoate, 8 reduced the paw volumes and the symptoms associated with the arthritis equally up to 10 to 15% at the dose of 100 mg/kg and this inhibition was dose dependent when dose was increased from 100 mg/kg to 300 mg/kg, which indicates that hexadecyl cis-9-tetradecenoate, 4 and hexadecyl cis-10-tetradecenoate, 8 are useful in alleviating the symptoms associated with the established arthritis.

Example 7

Evaluation of Hexadecyl cis-10-Tetradecenoate for Anti-arthritic Potential in Rats: The hexadecyl cis-10-tetradecenoate, 8 produced synthetically exemplified above in Scheme 2 was administered parenterally, particularly, by intraperitoneal route, either alone or in a compatible pharmaceutical carrier such as vegetable oils namely groundnut, sesame and cottonseed [for adjusting the dose volume of the active compound(s)] to male rats ranging in weight from 150 to 180 g. It should be noted that use of the mineral oil is not mandatory as the active compounds are oils themselves. The procedure as described in (Vogel's Drug Discovery and Evaluation Pharmacological assays, $2^{nd}$ ed, 2002, Springer Verlag, pages 802-803) was followed. Male Wistar-rats were divided into one control and two treated groups. All the animals in three groups received Freund's complete adjuvant (1 mg/rat). This day was designated as day 1. After a period of 24 hr, hexadecyl cis-10-tetradecenoate, 8 was administered at a dose of 300 mg/kg to one treated group and another treated group received 2.5 mg/kg of indomethacin (used as standard drug). Dosing was continued for 15 days (FIG. 3). Control group received the vehicle (mineral oil) without any drug. Paw volumes (left and right) were measured on every alternate day.

All the rats in the control group developed severe polyarthritis as indicated by the increase in the paw volumes. Whereas, rats treated with hexadecyl cis-10-tetradecenoate, 8 were protected from the polyarthritis. Around 80% of the animals in the hexadecyl cis-10-tetradecenoate treated group were protected from developing arthritis in a period of 21 days. The remaining 20% rats were protected from arthritis in a period of 32 days. It was also found that the effective range for protection of arthritis by hexadecyl cis-10-tetradecenoate, 8 was 0.1 to 1.0 gm/kg body weight of the animal. However doses less or more than this range were found to protect developments of the Freund's Complete Adjuvant induced poly arthritis in rats.

We claim:
1. A process for the preparation of two isomers of cetyl myristoleate namely hexadecyl cis-9-tetradecenoate and hexadecyl cis-10-tetradecenoate having general formula 1,

General formula 1

Where $n$ = 7 or 8
Where $m$ = 3 or 2 comprising the steps of:
a. cooling of an ester selected from the group consisting of oleic acid methyl ester and methyl undecenoate in the presence of an organic solvent at temperature ranges between −70 to −78° C.;
b. ozonolysis of cooled ester by bubbling of ozone for a period ranging between 60-90 min;
c. quenching the reaction with dimethyl sulphide (DMS) followed by stirring for a period ranging between 6-8 hr at temperature ranging between 25-35° C.;
d. evaporating the organic solvent and DMS from the reaction mixture as obtained in step (c) under vacuum to get a crude solid containing 1-al-methyl nonoate or 1-al-methyl deaconate depending upon the ester used in step (a);
e. dissolving crude solid containing 1-al-methyl nonoate or 1-al-methyl deaconate as obtained in step (d) in dry THF (tetra hydro furan);
f. simultaneously, dissolving triphenyl phosphine salt selected from the group consisting of n-pentyl-triphenyl phosphonium salt and n-butyl-triphenyl phosphonium salt in dry THF and cooled to a temperature ranging between 0-5° C. and followed by addition of n-butyl lithium;
g. stirring the reaction mixture as obtained in step (f) for a period ranging between 30-60 min to obtain an orange solution;
h. adding solution of crude solid in dry THF as obtained in step (e) into the solution of triphenyl phosphine salt in dry THF as obtained in step (f) followed by refluxing for a period of 0.3-8 hrs;
i. removing THF from the reaction mixture as obtained in step (h) under reduced pressure to get residue;
j. adding water in the residue as obtained in step (i) and followed by extraction with ether;
k. removing ether under vacuum to get the residue followed by carrying, out purification using column chromatography using hexane and ethyl acetate (98:2) as eluent to get cis-9-myristoleate and cis-10-myristoleate depending upon the ester used in step (a) and triphenyl phosphine salt used in step (f);
l. transesterifying myristoleate as obtained in step (k) with cetyl alcohol in the presence of enzyme selected from the group consisting of Lipozyme TL IM and Novozyme 435 at temperature ranging between 65-70° C. for a period ranging between 8 to 10 hr;

m. separating enzyme by filtration and evaporating the solvent to get the crude product having respective isomer of cetyl myristoleate;

n. purifying the crude product as obtained in step (l) by column chromatography to obtain pure cetyl myristoleate of formula 1.

2. A process as claimed in step (a) claim 1, wherein the organic solvent used in step (a) is dichloromethane or chloroform.

3. A process as claimed in claim 1, wherein oleic acid methyl ester used in step (a) and n-pentyl-triphenyl phosphonium salt used in step (t) for the preparation of cis-9-tetradecenoate.

4. A process as claimed in claim 1, wherein methyl undecenoate used in step (a) and n-butyl-triphenyl phosphonium salt used in step (f) for the preparation of cis-10-tetradecenoate.

5. Hexadecyl cis-10-tetradecenoate for use in treating inflammation and adjuvant-induced arthritis.

6. Hexadecyl cis-10-tetradecenoate for use in treating inflammation and edema of the animals up to 36% at a dose 400 mg/kg body wt.

7. Hexadecyl cis-10-tetradecenoate for use in reducing arthritis up to 10 to 15% at the dose of 100 mg/kg body wt.

8. Hexadecyl cis-10-tetradecenoate for use inblocking inflammation and reducing adjuvant-induced arthritis being effective for 21 days in 80% rats and for 32 days in 20% rats.

* * * * *